(12) United States Patent
Greene

(10) Patent No.: US 8,544,480 B1
(45) Date of Patent: Oct. 1, 2013

(54) DENTAL CARE KIT ASSEMBLY

(76) Inventor: Vivian A. Greene, Rockford, IL (US)

( * ) Notice: Subject to any disclaimer, the term of this patent is extended or adjusted under 35 U.S.C. 154(b) by 23 days.

(21) Appl. No.: 13/066,754

(22) Filed: Apr. 25, 2011

(51) Int. Cl.
*A45D 44/18* (2006.01)

(52) U.S. Cl.
USPC .......................................................... 132/309

(58) Field of Classification Search
USPC ................ 132/308–311, 323–324; 220/4.01, 220/500, 660, 89.3, 63.5, 361, 362.2; 225/39, 225/91, 93, 56
See application file for complete search history.

(56) References Cited

U.S. PATENT DOCUMENTS

| | | | | |
|---|---|---|---|---|
| 1,975,852 | A * | 10/1934 | Laub | 401/162 |
| 2,634,025 | A | 4/1953 | Hausner | |
| 3,890,986 | A * | 6/1975 | Gerlich | 132/309 |
| 4,527,574 | A | 7/1985 | Manfredi | |
| D322,172 | S | 12/1991 | Cheng | |
| D336,567 | S | 6/1993 | Glover et al. | |
| 5,439,014 | A * | 8/1995 | Moussa | 132/311 |
| D364,274 | S | 11/1995 | Vasquez | |
| D402,812 | S | 12/1998 | Goff | |
| 5,865,195 | A * | 2/1999 | Carter | 132/309 |
| 6,484,732 | B1 * | 11/2002 | Simister | 132/309 |
| 6,782,999 | B1 * | 8/2004 | McCoy et al. | 206/223 |
| 7,201,172 | B2 * | 4/2007 | Nanda | 132/309 |
| 2005/0111905 | A1 | 5/2005 | Glover | |
| 2006/0070636 | A1 * | 4/2006 | Peters | 132/324 |
| 2006/0280548 | A1 | 12/2006 | Sharpe | |
| 2007/0183838 | A1 | 8/2007 | Umar | |

* cited by examiner

*Primary Examiner* — Robyn Doan
*Assistant Examiner* — Brianne Kalach

(57) ABSTRACT

A dental care kit assembly for providing portable, sanitary, easy to use dental care tools in a single convenient compartment includes a compartment having an interior, a closed end and an open end. A toothbrush has a head portion, bristles positioned on the head portion, and a handle portion. The handle portion has an interior toothpaste storage space. Toothpaste is positioned in the interior toothpaste storage space. The handle portion includes a compressible portion adjacent to the interior toothpaste storage space such that applying pressure to the compressible portion urges the toothpaste through apertures in the head portion. Floss is removably coupled to a floss holder. A cap member is selectively engageable to the compartment for storing the toothbrush and the floss holder in the interior of the compartment.

11 Claims, 3 Drawing Sheets

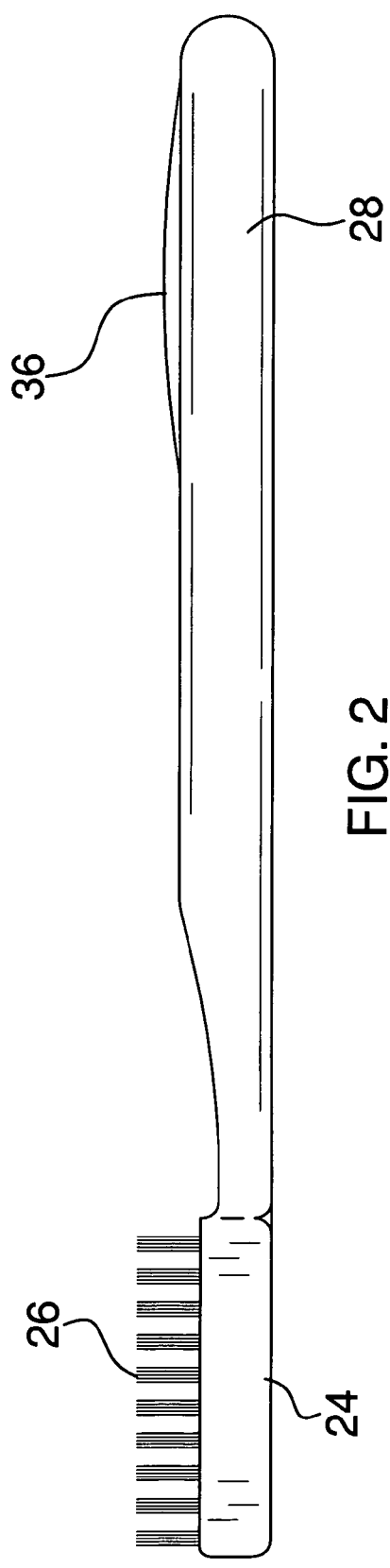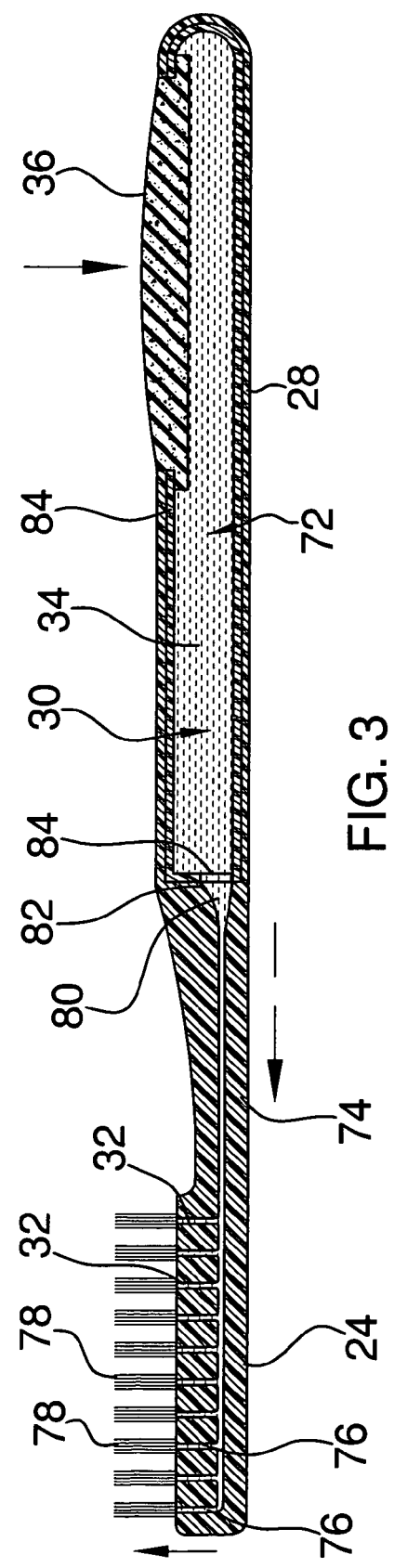

DENTAL CARE KIT ASSEMBLY

BACKGROUND OF THE DISCLOSURE

Field of the Disclosure

The disclosure relates to dental care kits and more particularly pertains to a new dental care kit for providing portable, sanitary, easy to use dental care tools in a single convenient compartment.

SUMMARY OF THE DISCLOSURE

An embodiment of the disclosure meets the needs presented above by generally comprising a compartment having an interior, a closed end and an open end. A toothbrush has a head portion, bristles positioned on the head portion, and a handle portion. The handle portion has an interior toothpaste storage space. Toothpaste is positioned in the interior toothpaste storage space. The handle portion includes a compressible portion adjacent to the interior toothpaste storage space such that applying pressure to the compressible portion urges the toothpaste through apertures in the head portion. Floss is removably coupled to a floss holder. A cap member is selectively engageable to the compartment for storing the toothbrush and the floss holder in the interior of the compartment.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

FIG. 2 is a side view of a toothbrush of an embodiment of the disclosure.

FIG. 3 is a cross-sectional view of the toothbrush of an embodiment of the disclosure taken along line 3-3 of FIG. 1.

DESCRIPTION OF THE PREFERRED EMBODIMENT

Figure 1:
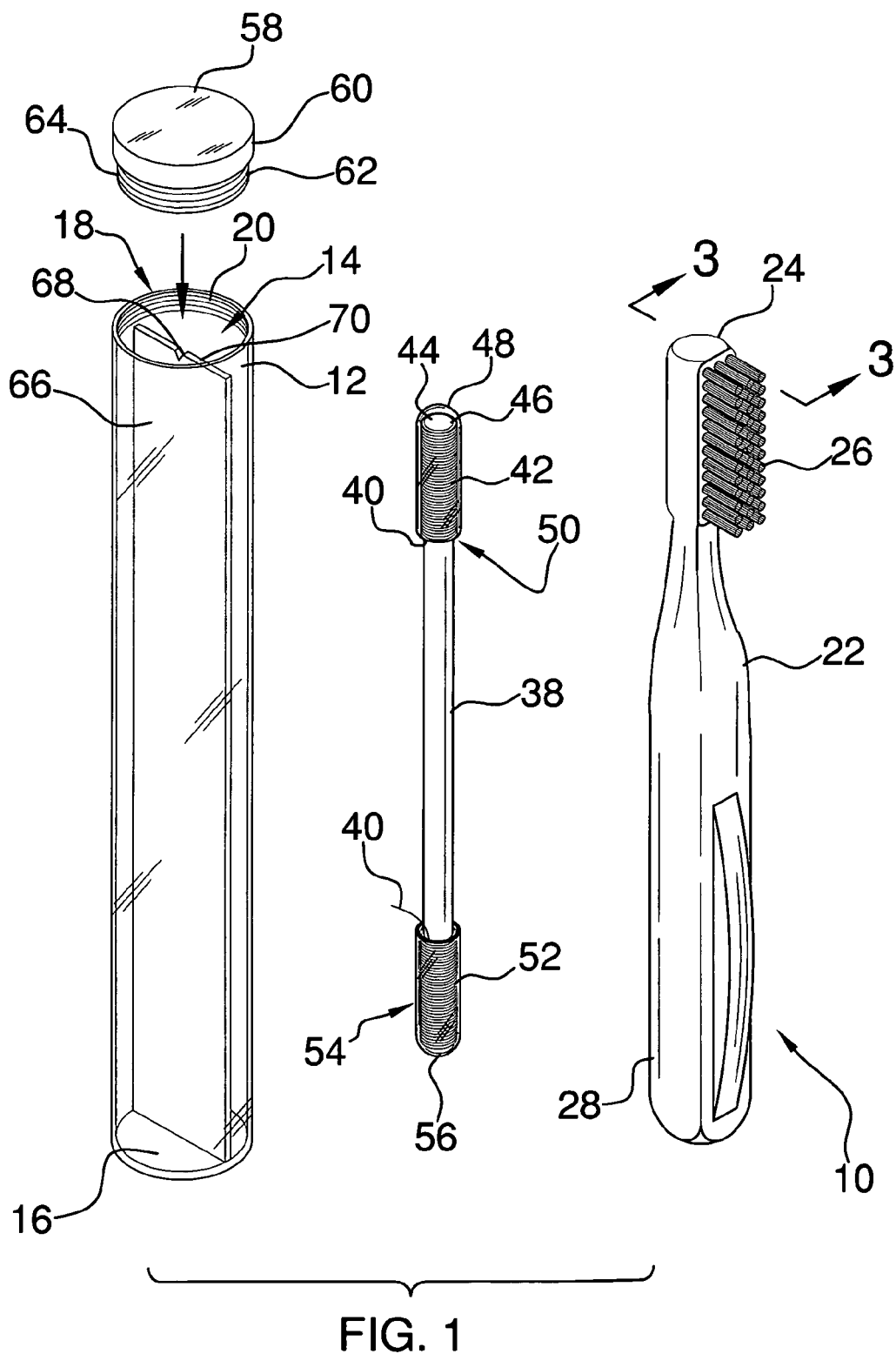
FIG. 1 is a front side top perspective view of a dental care kit assembly according to an embodiment of the disclosure.
Figure 4:
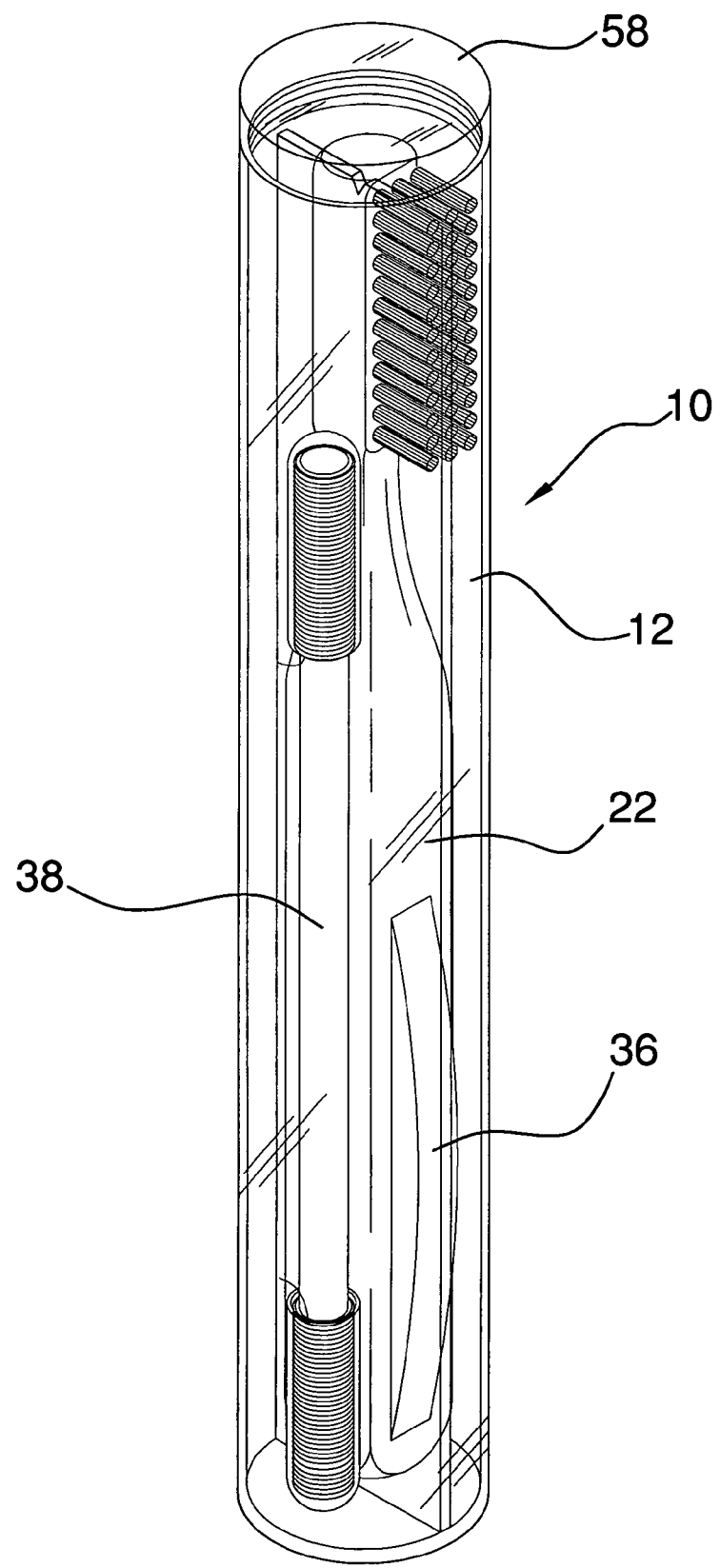
FIG. 4 is a top side front perspective view of an embodiment of the disclosure.

With reference now to the drawings, and in particular to FIGS. 1 through 4 thereof, a new dental care kit embodying the principles and concepts of an embodiment of the disclosure and generally designated by the reference numeral 10 will be described.

As best illustrated in FIGS. 1 through 4, the dental care kit assembly 10 generally comprises a transparent, tubular compartment 12 having an interior 14, a closed end 16, and an open end 18. The open end 18 has interior threading 20. A toothbrush 22 has a head portion 24, bristles 26 positioned on the head portion 24, and a handle portion 28.

The handle portion 28 has an interior toothpaste storage space 30. The head portion 24 includes a plurality of apertures 32 on the head portion 24 in environmental communication with the interior toothpaste storage space 30. Toothpaste 34 is positioned in the interior toothpaste storage space 30. The handle portion 28 includes a compressible portion 36 adjacent to the interior toothpaste storage space 30. Thus, squeezing the handle portion 28 to apply pressure to the compressible portion 36 urges the toothpaste 34 through the apertures 32 in the head portion 24.

A floss holder 38 and floss 40 are provided. A first portion of floss 42 is removably coupled to the floss holder 38. The first portion of floss 42 is wrapped around a first end 44 of the floss holder 38. A first floss cap 46 is positionable over the first portion of floss 42 for protecting the first portion of floss 42 while the first portion floss 42 is wrapped around the first end 44 of the floss holder 38. The first floss cap 46 has a closed end 48 and an open end 50 insertable over the first end 44 of the floss holder 38.

A second portion of floss 52 is wrapped around a second end 54 of the floss holder 38. A second floss cap 56 is positionable over the second portion of floss 52 for protecting the second portion of floss 52 while the second portion of floss 52 is wrapped around the second end 54 of the floss holder 38.

The floss holder 38 and the toothbrush 22 are insertable into the interior 14 of the compartment 12. A cap member 58 is selectively engageable to the compartment 12 for storing the toothbrush 22 and the floss holder 38 in the interior 14 of the compartment 12. The cap member 58 has a top portion 60 and a connection portion 62 extending from the top portion 58. The connection portion 62 has exterior threading 64 complimentary to the interior threading 20 of the open end 18. Thus, the connection portion 62 is couplable to the open end 18 of the compartment 12.

A divider 66 is positioned in the interior 14 of the compartment 12 for separating the floss holder 38 from the toothbrush 22 while the floss holder 38 and the toothbrush 22 are positioned in the interior 14 of the compartment 12. A notch 68 in a top 70 of the divider 66 is provided for facilitating cutting of the floss 40 into a desired length.

The interior toothpaste storage space 30 includes a main portion 72, a neck portion 74, and a plurality of feed channels 76. The bristles 26 are arranged into a plurality of bristle groups 78. Each of the feed channels 76 is aligned with an associated one of the bristle groups 78 to feed toothpaste 34 into the associated one of the bristle groups 78. The interior toothpaste storage space 30 further includes a constriction portion 80 between the neck portion 74 and the main portion 72 for facilitating distribution of toothpaste 34 through the feed channels 76. The constriction portion 80 includes a tapered wall portion 82 having an arcuate profile.

A frangible liner 84 is positioned in the interior toothpaste storage space 30 of the toothbrush 22. The toothpaste 34 is positioned in the frangible liner 84 such that compression of the compressible portion 36 breaks the frangible liner 84 to distribute the toothpaste 34 through the apertures 32 in the head portion 24.

In use, the toothbrush 22 and floss holder 38 are stored in the compartment 12. When desired, the cap member 58 is removed to provide access to the toothbrush 22 and the floss holder 38. The toothbrush 22 is used by squeezing the handle portion 28 to put pressure on the compressible portion 36. The frangible liner 84 breaks to release toothpaste 34 through the apertures 32 to the bristles 26. The floss 40 may be unwrapped from the floss holder 38 and cut to a desired length using the notch 68 in the divider 66.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A dental care kit assembly comprising:
   a compartment having an interior, a closed end and an open end;
   a toothbrush having a head portion, bristles positioned on said head portion, and a handle portion;
   wherein said handle has an interior toothpaste storage space;
   wherein said head portion includes a plurality of apertures on said head portion in environmental communication with said interior toothpaste storage space;
   toothpaste positioned in said interior toothpaste storage space;
   wherein said handle portion includes a compressible portion adjacent to said interior toothpaste storage space whereby squeezing said handle portion to apply pressure to said compressible portion urges said toothpaste through said apertures in said head portion, said toothpaste being urged through said apertures in said head portion when said compressible portion is squeezed regardless of the orientation of said toothbrush;
   a floss holder removably inserted into said interior of said compartment;
   floss removably coupled to said floss holder;
   said toothbrush being removably inserted into said interior of said compartment;
   a cap member selectively engageable to said compartment for storing said toothbrush and said floss holder in said interior of said compartment;
   a divider positioned in said interior of said compartment for separating said floss holder from said toothbrush while said floss holder and said toothbrush are positioned in said interior of said compartment; and
   a notch in a top of said divider for facilitating cutting of said floss into a desired length, said notch being positioned in said interior of said compartment.

2. The dental care kit assembly of claim 1, further comprising:
   wherein said floss is wrapped around a first end of said floss holder; and
   a floss cap positionable over said floss for protecting said floss while said floss is wrapped around said first end of said floss holder.

3. The dental care kit assembly of claim 2, wherein said floss cap has a closed end and an open end insertable over said first end of said floss holder.

4. The dental care kit assembly of claim 1, further comprising:
   said compartment being tubular;
   said open end having interior threading;
   said cap member having a top portion and a connection portion extending from said top portion; and
   said connection portion having exterior threading complimentary to said interior threading of said open end whereby said connection portion is couplable to said open end of said compartment.

5. The dental care kit assembly of claim 1, wherein said compartment is transparent.

6. The dental care kit assembly of claim 2, further comprising:
   a second portion of floss wrapped around a second end of said floss holder; and
   a second floss cap positionable over said second portion of floss for protecting said second portion of floss while said second portion of floss is wrapped around said second end of said floss holder.

7. The dental care kit assembly of claim 1, further comprising:
   said interior toothpaste storage space includes a main portion, a neck portion, and a plurality of feed channels;
   wherein said bristles are arranged into a plurality of bristle groups; and
   wherein each of said feed channels is aligned with an associated one of said bristle groups to feed toothpaste into said associated one of said bristle groups.

8. The dental care kit assembly of claim 7, wherein said interior toothpaste storage space further includes a constriction portion between said neck portion and said main portion for facilitating distribution of toothpaste through said feed channels.

9. The dental care kit assembly of claim 8, wherein said constriction portion includes a tapered wall portion having an arcuate profile.

10. The dental care kit assembly of claim 1, further comprising:
    a frangible liner positioned in said interior space of said toothbrush; and
    wherein said toothpaste is positioned in said frangible liner such that compression of said compressible portion breaks said frangible liner to distribute said toothpaste through said apertures in said head portion.

11. A dental care kit assembly comprising:
    a compartment having an interior, a closed end and an open end;
    a toothbrush having a head portion, bristles positioned on said head portion, and a handle portion;
    wherein said handle has an interior toothpaste storage space;
    wherein said head portion includes a plurality of apertures on said head portion in environmental communication with said interior toothpaste storage space;
    toothpaste positioned in said interior toothpaste storage space;
    wherein said handle portion includes a compressible portion adjacent to said interior toothpaste storage space whereby squeezing said handle portion to apply pressure to said compressible portion urges said toothpaste through said apertures in said head portion, said toothpaste being urged through said apertures in said head portion when said compressible portion is squeezed regardless of the orientation of said toothbrush;
    a floss holder;
    a first portion of floss removably coupled to said floss holder;

wherein said first portion of floss is wrapped around a first end of said floss holder;
a first floss cap positionable over said first portion of floss for protecting said first portion of floss while said first portion floss is wrapped around said first end of said floss holder;
wherein said first floss cap has a closed end and an open end insertable over said first end of said floss holder;
a second portion of floss wrapped around a second end of said floss holder;
a second floss cap positionable over said second portion of floss for protecting said second portion of floss while said second portion of floss is wrapped around said second end of said floss holder;
wherein said first end of said floss holder is integrally formed with said second end of said floss holder;
wherein said floss holder and said toothbrush are insertable into said interior of said compartment;
a cap member selectively engageable to said compartment for storing said toothbrush and said floss holder in said interior of said compartment;
a divider positioned in said interior of said compartment for separating said floss holder from said toothbrush while said floss holder and said toothbrush are positioned in said interior of said compartment;
a notch in a top of said divider for facilitating cutting of said floss into a desired length, said notch extending downwardly into said top of said divider, said notch being positioned in said interior of said compartment;
said compartment being tubular;
said open end having interior threading;
said cap member having a top portion and a connection portion extending from said top portion;
said connection portion having exterior threading complimentary to said interior threading of said open end whereby said connection portion is couplable to said open end of said compartment;
wherein said compartment is transparent;
said interior toothpaste storage space includes a main portion, a neck portion, and a plurality of feed channels;
wherein said bristles are arranged into a plurality of bristle groups;
wherein each of said feed channels is aligned with an associated one of said bristle groups to feed toothpaste into said associated one of said bristle groups;
wherein said interior toothpaste storage space further includes a constriction portion between said neck portion and said main portion for facilitating distribution of toothpaste through said feed channels;
wherein said constriction portion includes a tapered wall portion having an arcuate profile;
a frangible liner positioned in said interior space of said toothbrush; and
wherein said toothpaste is positioned in said frangible liner such that compression of said compressible portion breaks said frangible liner to distribute said toothpaste through said apertures in said head portion.

* * * * *